United States Patent [19]
Qureshi et al.

[11] Patent Number: 5,757,419
[45] Date of Patent: May 26, 1998

[54] INSPECTION METHOD AND APPARATUS FOR TANKS AND THE LIKE

[76] Inventors: Iqbal Qureshi; George R. McNulty, both of 10910 Briggs Rd., Cleveland, Ohio 44111

[21] Appl. No.: 759,070

[22] Filed: Dec. 2, 1996

[51] Int. Cl.⁶ .................................. H04N 7/18; H04N 9/47
[52] U.S. Cl. ........................... 348/82; 348/84; 901/15
[58] Field of Search ........................ 348/82, 83, 84, 348/85; 901/15; H04N 7/18, 9/47

[56] References Cited

U.S. PATENT DOCUMENTS

| | | | |
|---|---|---|---|
| H1115 | 12/1992 | Nichbar | 165/11.1 |
| 3,780,571 | 12/1973 | Wiesener | 348/83 |
| 3,852,527 | 12/1974 | McQuivey | 348/85 |
| 4,302,772 | 11/1981 | Gillot | 348/82 |
| 4,693,664 | 9/1987 | Schweiker | 414/735 |
| 4,728,974 | 3/1988 | Nio et al. | 354/81 |
| 4,798,341 | 1/1989 | Gimple | 239/694 |
| 4,804,038 | 2/1989 | Klahn et al. | 165/11.2 |
| 4,835,450 | 5/1989 | Suzuki | 318/568.13 |
| 4,881,177 | 11/1989 | McClean et al. | 364/513 |
| 4,905,913 | 3/1990 | Frikker | 239/751 |
| 4,941,182 | 7/1990 | Patel | 382/1 |
| 5,055,755 | 10/1991 | Ozawa et al. | 318/568.11 |
| 5,175,018 | 12/1992 | Lee et al. | 427/8 |
| 5,184,051 | 2/1993 | Schweiker et al. | 318/568 |
| 5,248,341 | 9/1993 | Berry, Jr. et al. | 118/698 |
| 5,518,553 | 5/1996 | Moulder | 134/22.18 |
| 5,604,532 | 2/1997 | Tillmanns | 384/84 |

*Primary Examiner*—Tommy P. Chin
*Assistant Examiner*—Nhon T. Diep
*Attorney, Agent, or Firm*—Pearne, Gordon, McCoy and Granger LLP

[57] ABSTRACT

A method and apparatus for remotely visually inspecting the interior of an elongated tank. The apparatus includes an articulated arm which extends into the tank through an access opening and is adapted to pivot at successive joints by operation of associated servomotors to enable it to follow a path along the axis of the tank. A TV camera is carried on the lead end of the arm and scans the interior of the tank through 360° rotation about the tank axis. The arm carries the camera to the zones where the tank end walls are joined to the sidewall for viewing the zones from advantageous lines of view.

1 Claim, 8 Drawing Sheets

INSPECTION METHOD AND APPARATUS FOR TANKS AND THE LIKE

BACKGROUND OF THE INVENTION

The invention relates to methods and apparatus for remote visual inspection of the internal surfaces of a tank.

PRIOR ART

Railroad tank cars are periodically internally inspected for corrosion that could otherwise lead to a loss of the product being transported through leakage or a catastrophic rupture in the tank wall. A loss of liquid by a corrosion failure of a tank can foul the environment and pose health and safety hazards to personnel and nearby residents. Corrosion can occur prematurely where a bulk chemical is mistakenly introduced into a tank that is not suited for contact with such chemical, or is not provided with a protective coating resistant to the chemical in question or where the chemical is reactive with the residue of a previously transported bulk chemical. In such cases, there is a risk that the tank surfaces, particularly the weld areas, will be chemical attacked thereby subjecting the same to premature or accelerated corrosion.

Conventionally, tank cars are visually inspected by a worker who climbs into the tank and examines its interior surface. This inspection can be dangerous because harmful or toxic vapors may exist in the tank. Before entry by a worker, an effort may be made to purge the tank of hazardous vapors. It is the custom for two workers to perform the inspection; one worker enters the tank and the other worker remains outside of the tank to assist the first worker if he is impaired or overcome by any vapors or fumes in the tank. It is relatively expensive to inspect a tank because two workmen are involved and because of the safety precautions required to protect the workers that must be performed.

SUMMARY OF THE INVENTION

The invention provides a way of remotely visually inspecting the interior of a tank such as a railroad tank car in a methodical, precise and recordable manner without subjecting personnel to risks involved in personally entering the tank. The invention utilizes a TV camera to visually scan the interior of a tank in an efficient methodology. The video signal produced by the camera can be displayed on a monitor for real time simultaneous study by a technician and can be stored in a record medium, such as a magnetic tape, for later viewing at any desired scanning rate, including stop action. The visual record affords a complete maintenance record and data for future reference.

As disclosed, the camera is carried into a tank by an automatically controlled support. The support enables the camera to move along the longitudinal axis of the tank so that it can view various internal surface areas from a line of sight that is perpendicular or nearly perpendicular to such areas.

As disclosed, the camera support is in the form of an articulated segmented arm that is lowered vertically into a tank, typically through a manway, and is then actuated to pivot at successive joints to carry the camera along a longitudinal path in the tank. Preferably, the camera lens rotates about the axis of the path so that it scans all of the tank sidewall surrounding it through progressive axial locations. The camera lens is capable of rotating in the manner of a gimbal about an axis perpendicular to the longitudinal axis of the tank through a large angle so that it is capable of viewing the internal surface of the end wall of the tank from a line of sight perpendicular or nearly perpendicular to such surface.

In the preferred embodiment, the camera supporting arm is in the form of a series of segments that each have a length approximating the radius of the sidewall of the tank. This construction enables the arm to be readily and efficiently extended radially into a tank and then extended along the tank axis. A laser distance measuring device adjacent the camera lens enables a controller to accurately position the arm along the axis of the tank. The laser measuring device also enables the system to detect and measure dents, protrusions or creases that may have been accidentally created in the tank during service and which could pose a failure hazard.

DESCRIPTION OF THE PREFERRED EMBODIMENT

Figure 1:
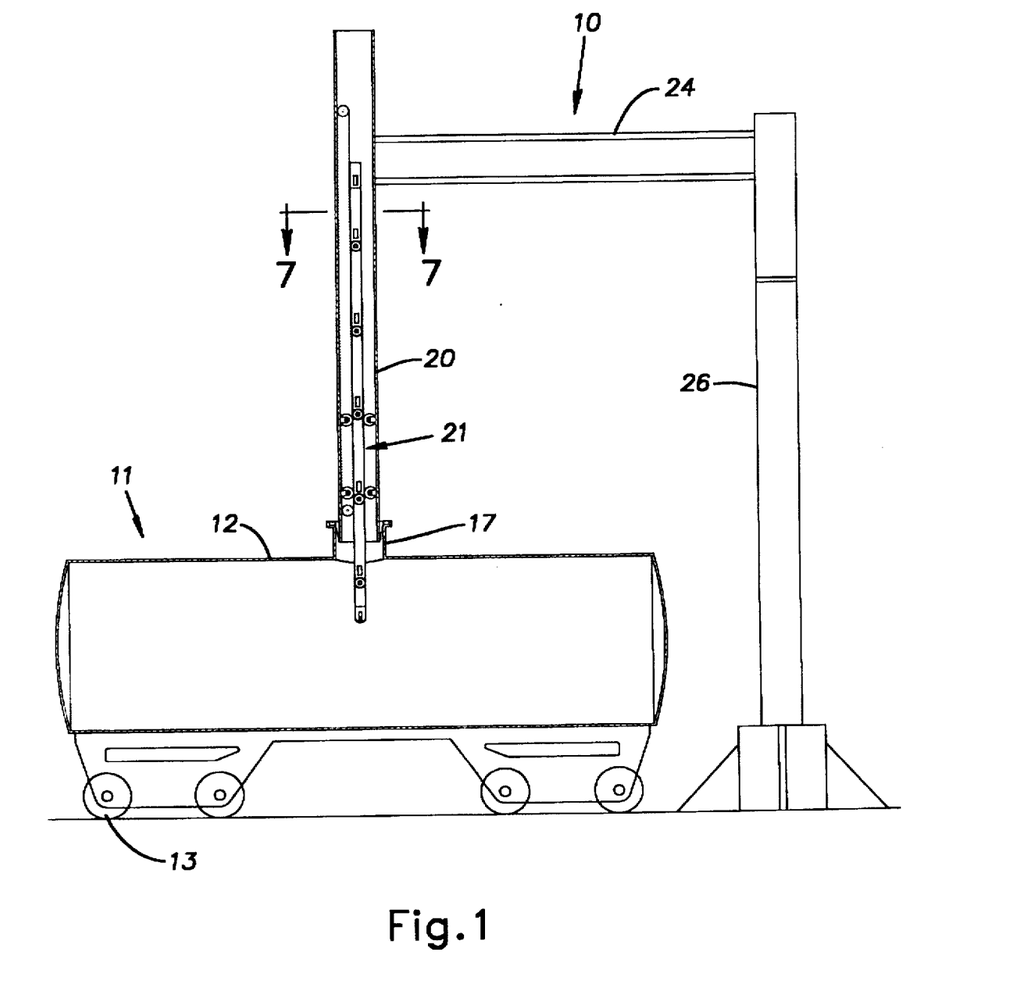
FIG. 1 is a somewhat schematic elevational view of components of a system for remote visual inspection of the interior of a tank at the beginning of the insertion by an inspection camera.
Figure 2:
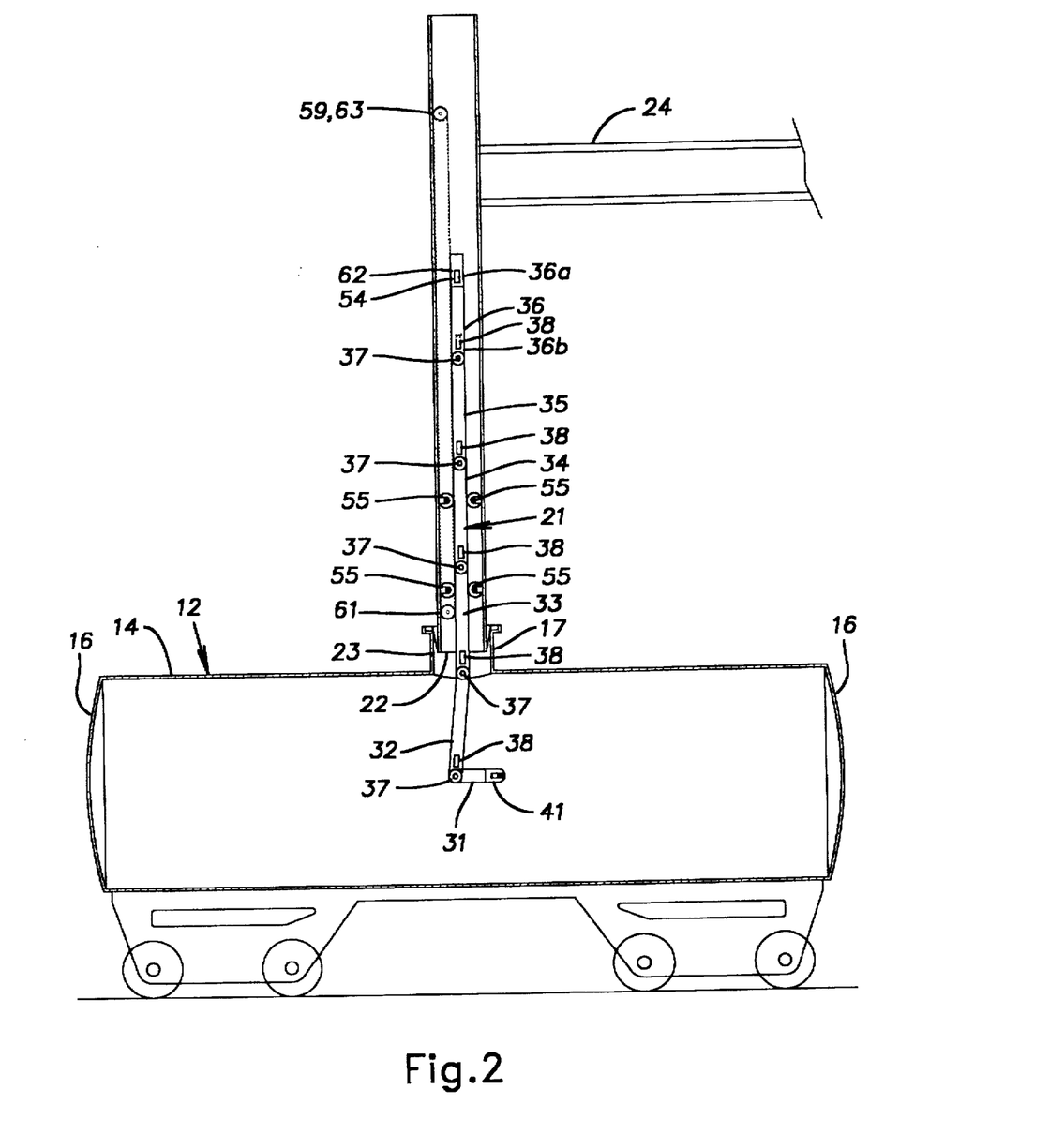
FIGS. 2 through 6, inclusive, are fragmentary schematic views showing a sequence of extension of an articulated segmented arm that supports the inspection camera in a path along the axis of the tank.
Figure 3:
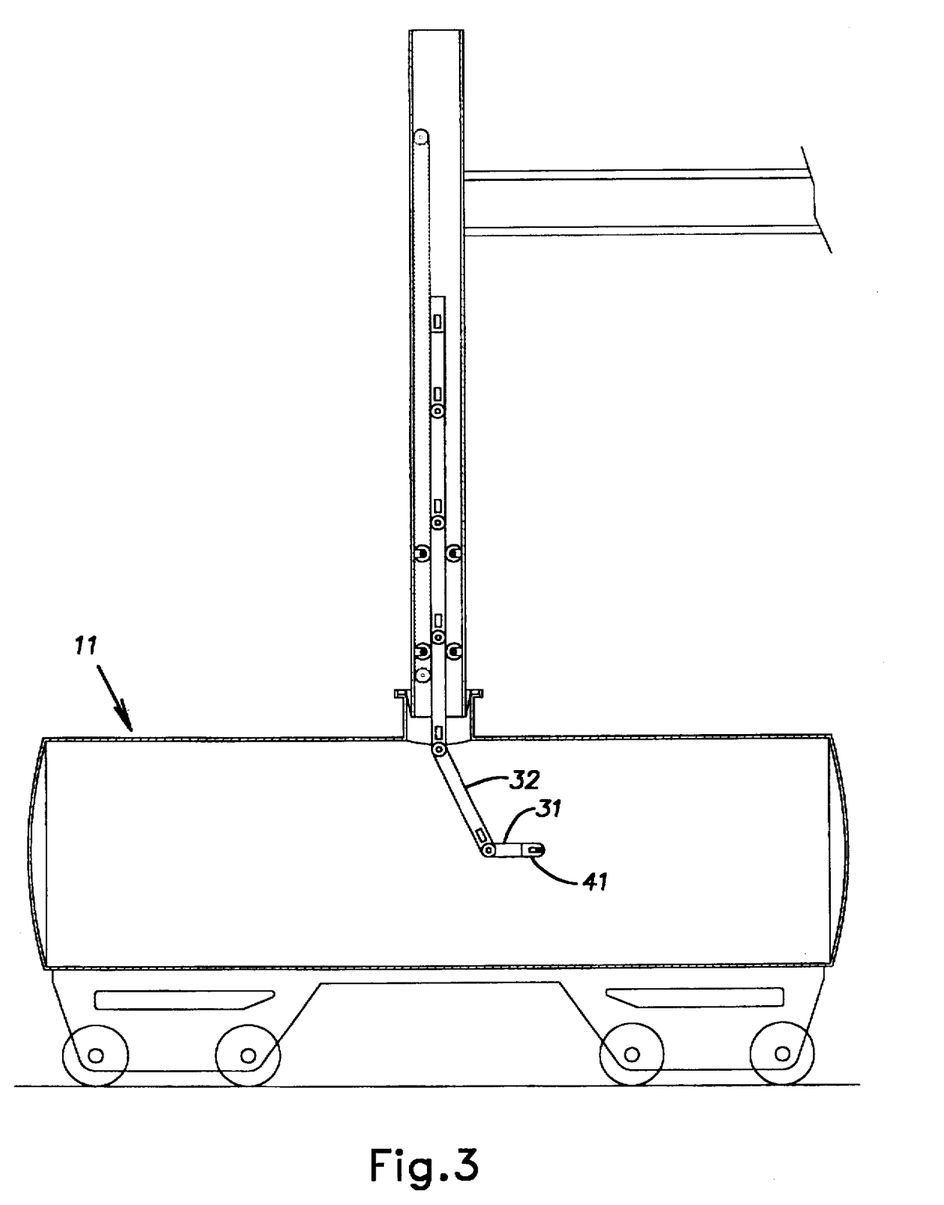
Figure 4:
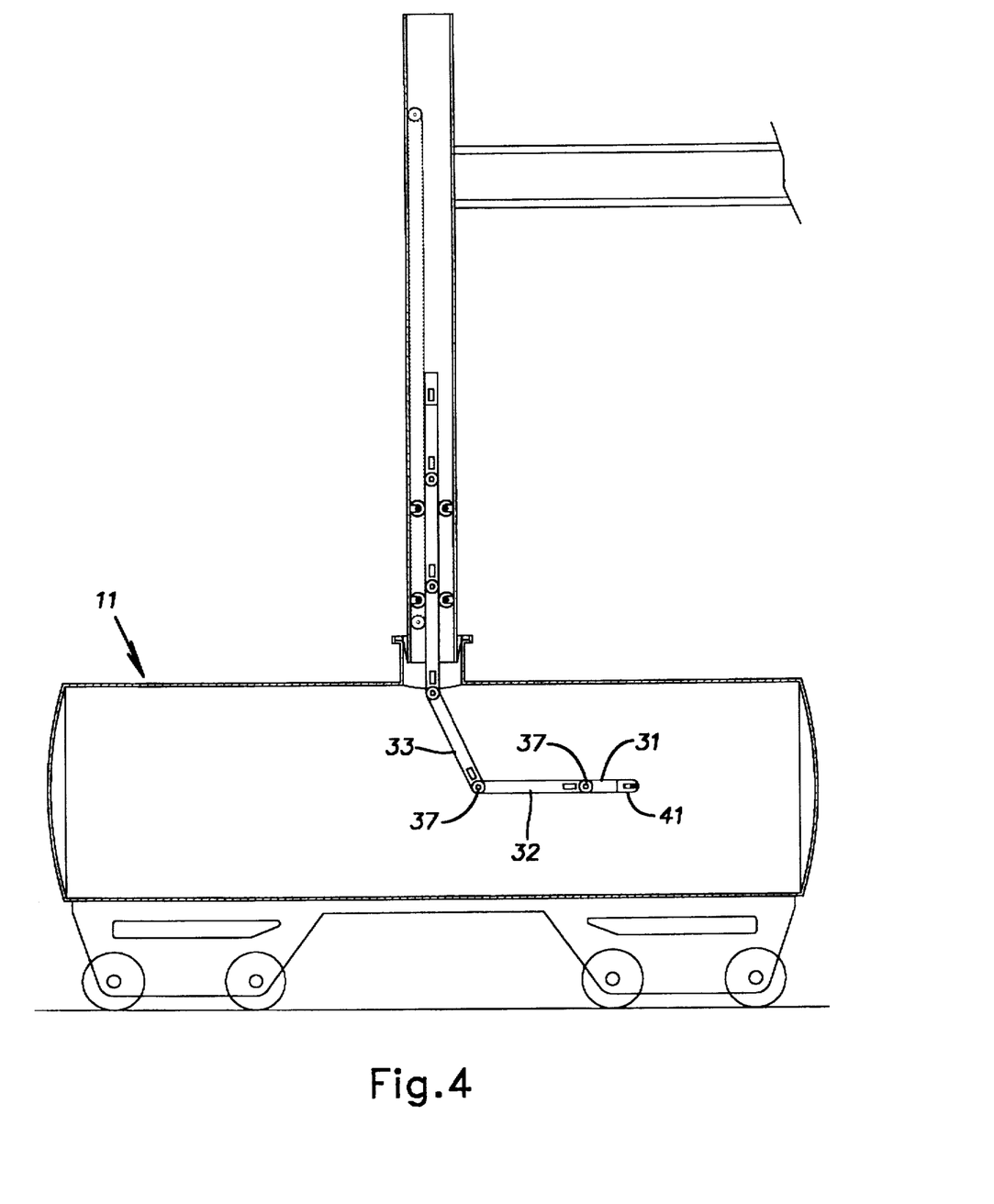
Figure 5:
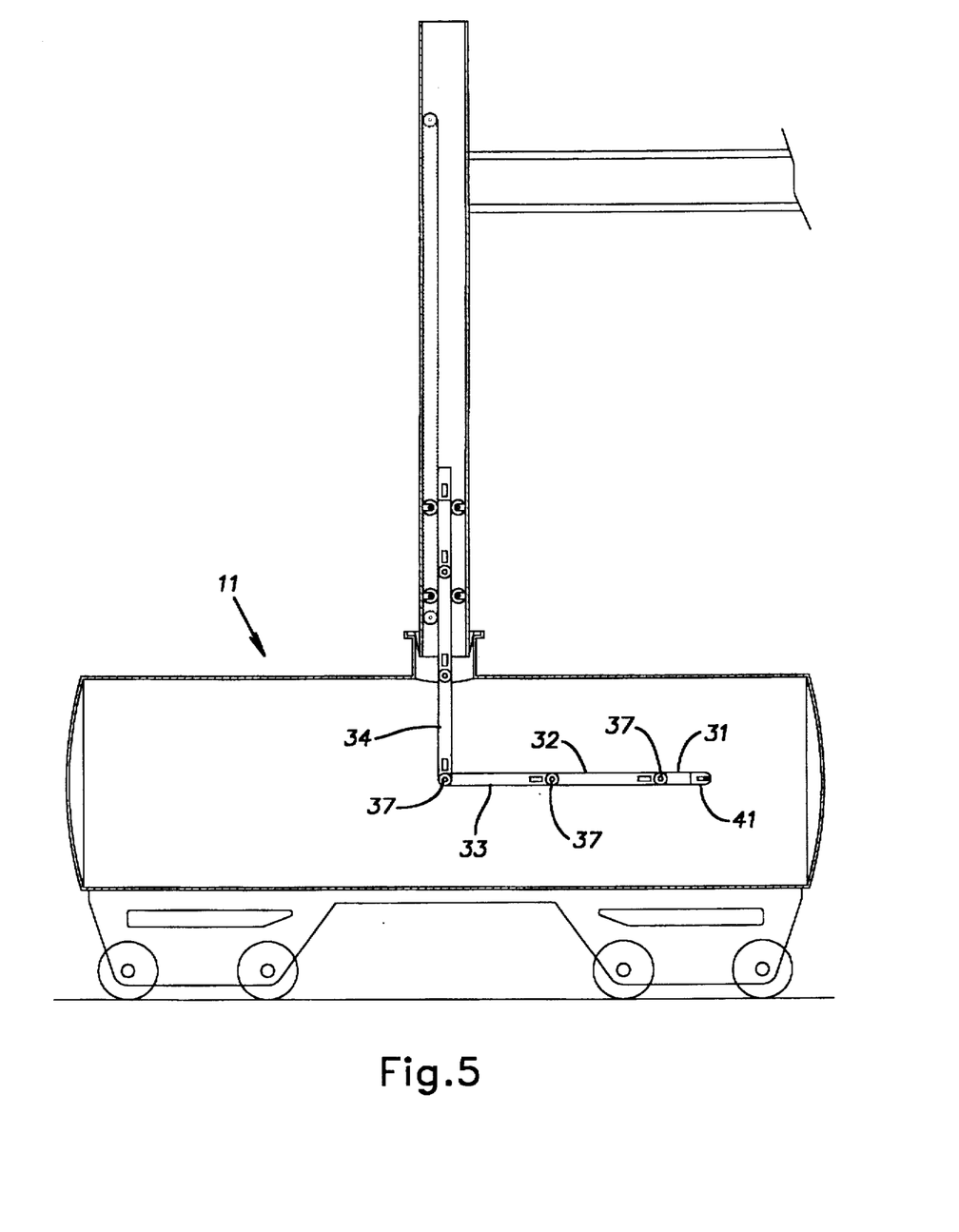
Figure 6:
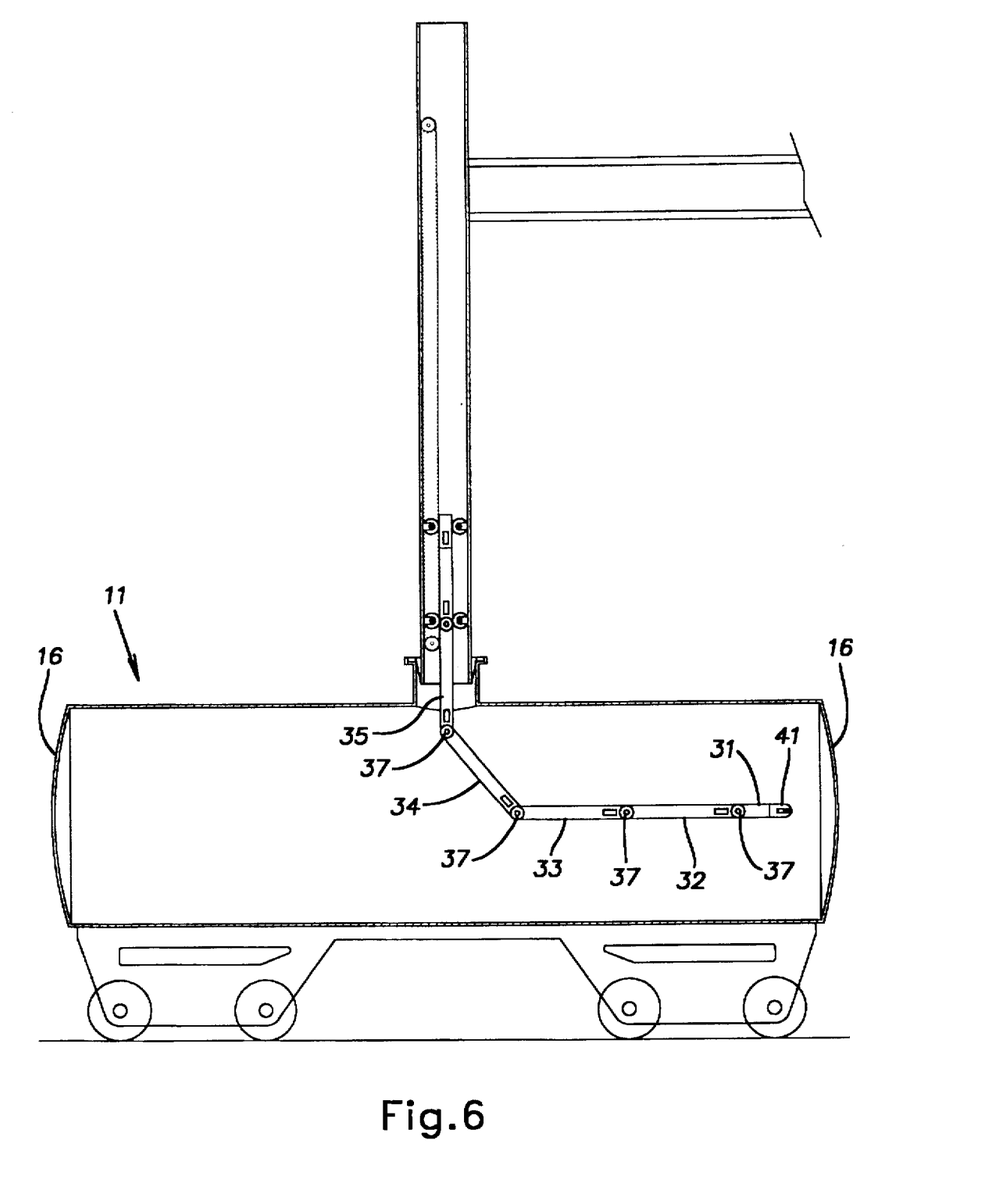

FIG. 1 schematically illustrates components of as system 10 capable of remotely visually inspecting the interior of a large enclosed space such as that of a railroad tank car 11. It will be understood that the invention has other applications from the following description such as inspecting highway tank cars, underground and above-ground storage tanks as well as other closed chambers. A typical railroad tank car 11 has a cylindrical tank 12 carried on track engaging wheels 13. Normally, the tank 12 has a cylindrical sidewall 14 and domed end walls 16. The tank 12 is conventionally fabricated as a weldment of steel sheet or plate stock. A typical tank is between about 8 to 12 feet in diameter and about 35 to 50 feet in length. It will be understood that the invention is useful for inspecting tanks that are non-cylindrical such as those having an oval cross-section. Periodically the interior of the tank is inspected particularly at weld joints of the steel sheets from which it is fabricated to locate any corrosion or other degradation. It is particularly important that the joint between an end wall 16 and the sidewall 14 be clearly observed. Typically, the tank 12 has a manway 17 on its top side midway between the end walls 16 with a minimum inside diameter of about 14 inches to afford access for a workman to enter the tank.

The system 10 includes a vertically oriented support 20 carrying an inspection arm 21. The illustrated support 20 is in the form of a circular hollow receiver or casing having a lower end provided with a conical guide 23 to allow the support casing to self-align with the mouth of the manway 17. In the illustrated embodiment, the support casing 20 is carried by a cantilever beam 24 extending horizontally from a mast 26. Various constructions can be used to align the lower end 22 of the support casing 20 with the manway 17. For example, the beam 24 can be moved vertically on the mast with a suitable manually or automatically controlled jack. Additionally, the beam 24 and support casing 20 can be rotated about the axis of the mast 26 either manually or automatically to horizontally register the lower end 22 of the support casing with the manway or to swing the support casing clear of the path of the railroad car 11. It will also be understood that the support casing 20 can alternatively be transported by a mobile crane or by a truck, for example, to and from a tank to be inspected.

Figures 7, 8:
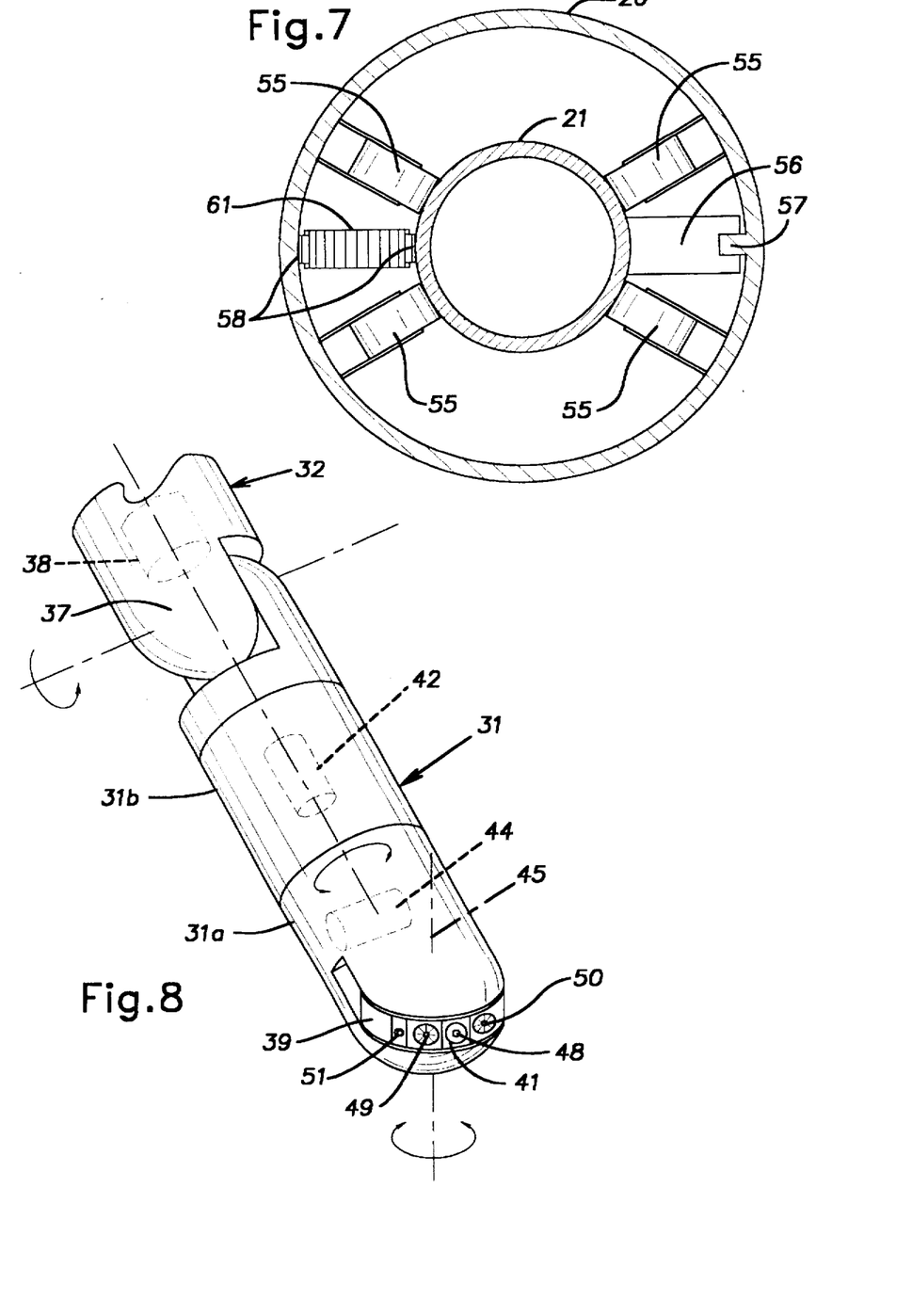
FIG. 7 is a cross-sectional view, taken in the plane 7—7 indicated in FIG. 1 illustrating construction details of the inspection device.
FIG. 8 is a schematic perspective view of the lead end of the inspection arm and a camera carrier.

The inspection arm 21 is comprised of a series of articulated segments 31 through 36, inclusive. The adjacent ends of the segments 36 are connected at a joint 37 that limits pivotal movement about a single axis transverse to the longitudinal axis of the respective segments 31–36. The pivot axis of all the joints 37 are parallel to one another. Each joint 37 has an associated servomotor 38 capable of establishing the relative angular orientation of the respective pair of segments 31, 32; 32, 33, etc. about the joint pivot axis. As shown, the majority of the segments have a length that is approximately equal to the radius of the cylindrical sidewall 14, that is, one-half the height of the interior of the horizontally elongated tank 12. The leading end of the arm 21 has a short segment 31 on which a carrier 39 for a camera 41 is disposed. A servomotor 42 on the segment 31 is capable of rotating a distal end portion 31a of the segment 31 and, therefore, the camera carrier 39 relative to a proximal portion 31b adjacent to the associated joint 37 through 360° of rotation. The camera carrier or mount 39 has a construction similar to a gimbal and is capable of rotating approximately 270° about an axis 45 that intersects and is perpendicular to the longitudinal axis of the lead end segment 31. A servomotor, indicated at 44, in the segment 31 adjusts the angular position of the carrier 39 relative to the segment 31 about this axis 45 (FIG. 8).

The TV camera 41 provides a remote visual inspection device having a light receiving viewing lens 48. The camera 41 and lens 48 are carried on the gimbal support or carrier 39. Preferably, the camera is a color unit with remote focus and remote zoom controls. Two visible light lamps, 49, 50, are aligned with the field of view of the lens 48; one lamp 49 is a flood lamp, while the other lamp 50 is a focus lamp. Adjacent the lens 48 is a non-contact distance measuring device in the form of a laser unit 51. The laser measuring device 51 is aligned in parallel with the line of sight of the viewing lens 48.

An upper or trailing segment 36 of the arm 21 has two sections 36a, 36b capable of rotation relative to one another about their common longitudinal axis. This rotation which is limited to a total of 30°, i.e. ±15°, for example, is accomplished by a servomotor 54. The upper section 36a is fixed against relative rotation in the casing 20 by a horizontal extension 56 that is rigidly connected to this section and that has a notch which slidingly engages opposite sides of a vertical key 57 fixed on the interior of the casing. An endless toothed belt 58 is trained over a pair of pulleys 59, 61, mounted for rotation at fixed vertically spaced locations on the interior of the casing 20. The belt 58 is fixed to the arm at a location designated 62 on the non-rotating section 36a. A servomotor 63 drives the associated pulley 59 in rotation to control the position of the belt 58 and, therefore, the vertical position of the arm segment 36 to which the belt is fixed. The arm 21 is guided, in the casing 20, for vertical movement by rollers 55 rotatable on axes fixed in the casing.

Figure 9:
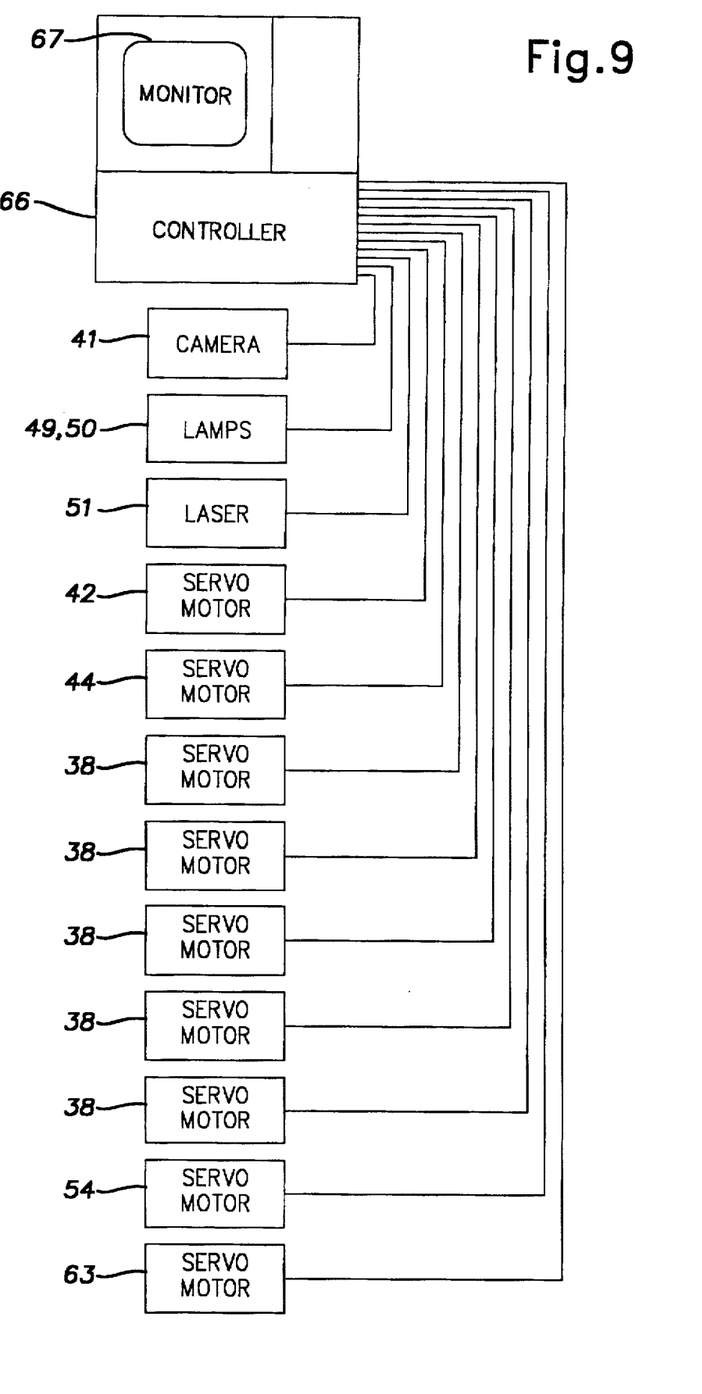
FIG. 9 is a schematic diagram of a controller and certain active components of the system.

The system 10 includes an electronic controller 66 interconnected with the various servomotors, camera, lamps, and laser measuring device by appropriate wires and ship rings, for example. The controller 66 can be in the form of a small computer with a keyboard, for example. A monitor 67 connected to the controller 66 displays a menu for the program or software used with the controller 66 and displays pictures imaged by the camera 41. The controller 66 includes a video recording system, preferably for magnetic tape, such as a helical scanning ½ inch color unit with four rotary video heads. The video recording system permits recording of the images scanned by the camera 41 and allows a playback of such images from the video tape. If desired, the controller 66 can include a color video printer to provide color videographs of selected inspection areas.

An example of a manner of operation of the system 10 is now described. The railroad tank car 11 is positioned so that its manway 17 is below the casing 20. It will be understood that initially the casing 20 is elevated somewhat from the position illustrated in the figures. When the car 11 is in place, the casing 20 is lowered onto the manway 17 by operation of a jack in the mast which can be accomplished manually or automatically under the direction of the controller 66. Seating of the alignment cone 23 on the lower end 22 of the casing 20 on the mouth of the manway 17 effects a coupling between these members. The servomotor 63 associated with the belt 58 is activated by the controller 66 to extend the arm 21 into the tank 12. The controller 66 is programmed to produce a suitable actuation of the vertical movement servomotor 63 as well as appropriate ones of the joint servomotors 38 to produce, ordinarily, a continuous sequence of motion between the stages depicted in FIGS. 1 through 6. It will be understood that when the casing 20 is first being coupled to the manway 17, the lower end of the arm 21 is fully within the casing.

The program followed by the controller 66 initially reverses the angle of the first full length segment 32 to position the camera 41 directly below the center of the manway 17, which can be the longitudinal center of the tank 12, with the axis of rotation of the leading arm segment 31 horizontal and at the vertical center of the tank 12. In this position, and thereafter, the camera 41 can be operated to view the interior surface of the tank in a general scanning action or in a close-up zoom action as determined by the controller 66 or manually by a technician working through the controller and viewing the monitor 67. The controller 66 and monitor 67 are typically remotely situated from the interior of the tank 12 and the monitor displays the images seen by the camera lens 48. Data produced by the camera 41 can be stored, for example, by the controller 66 on a video tape for proof of inspection and for future reference. The controller program dictates appropriate positions for the servomotors 38 at the joints 37 and the servomotor 63 at the belt pulley 59 to produce a smooth movement of the lead arm segment 31 and the camera mount or carrier 39 in a path parallel to the longitudinal central axis of the tank 12. During the time before the camera 41 has reached a location near an end wall 16, e.g. FIG. 6, the servomotor 42 in the segment 31 rotates the camera carrier or mount 39 about the longitudinal axis of the section 31 which, ideally, is coincident with the tank axis and the gimbal servomotor 44 is caused to point the camera lens 68 so that its line of sight is radial to the tank axis and generally perpendicular to the tank interior surface. The laser measuring device 51 typically is active when the camera is active and is aimed in the same direction as the camera.

Data from the laser device 51 is processed by the controller 66 to correct positioning errors of the arm 21 by adjustment of appropriate ones of the servomotors 38, 63 and 54 to keep the lead arm section 31 with the camera 41 on the longitudinal axis of the tank 12. Deviation of the lead arm section 31 from the tank axis in a horizontal plane is corrected by the controller 66 through operation of the servomotor 54 in the split upper arm section 36 where a lower portion 36b is rotated about a vertical axis relative to the upper section 36a. Deviation of the lead arm section 31 from the tank axis in a vertical plane is corrected by the controller 66 through operation of an appropriate one or more of the joint actuators or servomotors 38 and/or the vertical motion servomotor 63. The rate of travel of the lead end segment 31 along the axis of the tank and the rate of rotation of the camera about the axis of the lead arm segment 31 are determined by the definition, i.e. clarity required in the electronic images produced by the camera 41. The arm 21 progressively carries the camera eventually to a location adjacent the end wall (e.g. FIG. 6) where it can clearly scan the weld joining the end wall 16 to the sidewall 14. The end wall 16 is visually scanned by the camera 41 with the controller 66 causing the servomotor 42 to rotate the lead arm portion or section 31a and simultaneously causing the gimbal servomotor 44 to rotate the carrier or mount 39.

The other side of the tank 12, i.e. the left side of the tank as depicted in the drawings, is inspected after the above operations by withdrawing the arm 21 from the right side of the tank essentially by reversing the sequence depicted in FIGS. 2 through 6. Thereafter, the arm is extended to the left by reversing the rotations of the various joint servomotors 38 to produce a mirror image of the sequence depicted in FIGS. 2 through 6 thereby resulting in the arm 21 extending along the left side of the tank in essentially the same manner as that described above in connection with the right side. When the tank 12 is completely inspected, the arm 21 is withdrawn into the receiver casing 20 and the casing is elevated to decouple the casing guide 23 from the manway 17.

From the foregoing explanation, it will be understood that personnel do not have to enter the tank to accomplish a thorough visual inspection of the interior of the tank. The images observed by the camera 41 can be observed by qualified personnel at any time either when the camera is operating or at a later date. Still frames of images recorded by the camera can be produced in a known manner. The laser measuring device can detect distortion in the tank sidewall such as a dent, crease, or bulge.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

We claim:

1. A device for remotely visually inspecting the interior of an elongated tank comprising a support, a viewing device carried on the support and a unit for displaying images of the interior of the tank scanned by the viewing device exterior of the tank, the support including a rigid member capable of entering the tank through an access hole in the side of the tank in a radial direction and extending from the zone of the access hole along the axis of the tank to a point relatively remote from the access hole and adjacent an end of the tank, the viewing device being capable of scanning the full inner circumference of the tank sidewall while the viewing device is carried be the support axially from the zone of the access hole to a point adjacent an end wall of the tank, the support comprising a series of articulated segments, each one of said segments having a length approximately equal to one-half the vertical height of the tank measured from the access hole to a point opposite the access hole.

* * * * *